United States Patent [19]

Haag et al.

[11] 4,136,128

[45] * Jan. 23, 1979

[54] CATALYTIC ALKYLATION/TRANSALKYLATION

[75] Inventors: Werner O. Haag, Trenton; David H. Olson, Pennington, both of N.J.

[73] Assignee: Mobil Oil Corporation, New York, N.Y.

[*] Notice: The portion of the term of this patent subsequent to Jan. 24, 1995, has been disclaimed.

[21] Appl. No.: 851,334

[22] Filed: Nov. 14, 1977

Related U.S. Application Data

[63] Continuation-in-part of Ser. No. 580,864, May 27, 1975, Pat. No. 4,070,407, which is a continuation-in-part of Ser. No. 449,315, Mar. 8, 1974, abandoned.

[51] Int. Cl.$^2$ .................... C07C 3/52; C07C 3/62
[52] U.S. Cl. .................... 260/671 R; 260/672 T
[58] Field of Search .................... 260/671 R, 672 T

[56] References Cited

U.S. PATENT DOCUMENTS 4,070,407  1/1978  Haag et al. .................... 260/672 T Primary Examiner—C. Davis
Attorney, Agent, or Firm—Charles A. Huggett; Raymond W. Barclay

[57] ABSTRACT

A process is provided for alkylation or transalkylation of aromatic hydrocarbons by contacting same with an alkylating or transalkylating agent in a reaction zone maintained under alkylation/transalkylation effective conditions and in the presence of a catalyst comprising a crystalline aluminosilicate zeolite ZSM-35 and/or ZSM-38, said catalyst under said conditions being capable of affording a high and selective yield of desired alkyl-aromatic product while maintaining excellent aging properties.

15 Claims, No Drawings

CATALYTIC ALKYLATION/TRANSALKYLATION

CROSS-REFERENCE

This is a continuation-in-part of application Ser. No. 580,864, filed May 27, 1975, now U.S. Pat. No. 4,070,407, which was a continuation-in-part of application Ser. No. 449,315, filed Mar. 8, 1974, now abandoned.

BACKGROUND OF THE INVENTION

1. Field of the Invention

This invention is directed to the alkylation or transalkylation of aromatic hydrocarbons including aromatic hydrocarbons containing a non-polar substituent, e.g. benzene or toluene, with an alkylating or transalkylating agent, e.g. an olefin or a polyalkylaromatic hydrocarbon, wherein the alkylation or transalkylation is performed in the presence of a catalyst composition comprising a zeolite selected from the group consisting of ZSM-35, ZSM-38 and a combination thereof, said zeolite being characterized by long catalyst life, being capable of affording high selectivity to desired products, e.g. alkylaromatics, and being easily and effectively regenerated, when necessary, without substantial loss in activity.

2. Description of the Prior Art

Alkylation of aromatic hydrocarbon compounds employing certain crystalline aluminosilicate zeolite catalysts is known in the art. For instance, U.S. Pat. No. 3,251,897 describes liquid phase alkylation in the presence of crystalline aluminosilicates such as faujasite, heulandite, clinoptilolite, mordenite, dachiardite, zeolite X and zeolite Y. The temperature of such alkylation procedure does not exceed 600° F. for use of any of the aluminosilicates as catalyst.

Also, U.S. Pat. No. 2,904,607 shows alkylation of hydrocarbon compounds in the presence of certain crystalline aluminosilicate zeolites. The zeolites described for use in this patent are crystalline metallic aluminosilicates, such as, for example, magnesium aluminosilate. U.S. Pat. No. 3,562,345 shows transalkylation of toluene over a zeolite catalyst typified by mordenite, e.g. Zeolon (see comparative examples hereinafter presented). U.S. Pat. No. 3,668,264 shows alkylation of aromatic hydrocarbons over several synthetic and naturally occurring zeolites, not including synthetic zeolite ZSM-35 and ZSM-38. One naturally occurring zeolite mentioned as suitable in the latter patent is ferrierite (see comparative examples hereinafter presented).

U.S. Pat. Nos. 3,631,120 and 3,641,177 describe a liquid phase process for alkylation of aromatic hydrocarbons with olefins in the presence of certain zeolites. U.S. Pat. No. 3,631,120 discloses use of an ammonium exchanged, calcined zeolite having a silica to alumina mole ratio of between 4.0 and 4.9. U.S. Pat. No. 3,641,177 discloses use of a zeolite catalyst activated in a particular manner.

Unfortunately, while many of the crystalline aluminosilicate catalysts proposed for such alkylation methods provide satisfactory initial yields of desired products, for the most part, their catalytic aging properties are not sufficiently good enough to warrant commercial application. Hence, it is of advantage to provide a satisfactory process for alkylating or transalkylating aromatic hydrocarbons, depending upon whether an alkylating or transalkylating agent is employed, using a crystalline aluminosilicate zeolite catalyst which has improved aging properties, i.e. maintains alkylation or transalkylation in high yield over a long, commercially attractive period of time, heretofore lacking in the art.

SUMMARY OF THE INVENTION

This invention contemplates a process for effecting alkylation or transalkylation of aromatic hydrocarbons, including aromatic hydrocarbons containing a non-polar substituent, which comprises contacting an aromatic hydrocarbon charge with an alkylating agent or a transalkylating agent under conditions effective for accomplishing said alkylation or transalkylation including a reactor inlet temperature between about 37° C. and about 650° C., depending upon whether the process is alkylation or transalkylation, as distinguished hereinafter, a pressure between atmospheric and 3000 psig, employing a mole ratio of aromatic hydrocarbon to alkylating agent or transalkylating agent in the approximate range of 1:3 to 20:1 and a total feed weight hourly space velocity between about 0.5 $hr^{-1}$ and about 1000 $hr^{-1}$, in the presence of a catalyst comprising a crystalline aluminosilicate zeolite ZSM-35 and/or ZSM-38, each characterized by a unique specified X-ray powder diffraction pattern. The above weight hourly space velocity is based upon the weight of crystalline aluminosilicate.

DESCRIPTION OF SPECIFIC EMBODIMENTS

Zeolites which may be included in the catalyst composition for use in the present process include ZSM-35 and ZSM-38.

ZSM-35 is described by U.S. Pat. No. 4,016,245, the disclosure of which is incorporated herein by reference. This zeolite can be identified, in terms of mole ratios of oxides and in the anhydrous state, as follows:

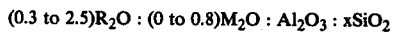
(0.3 to 2.5)$R_2O$ : (0 to 0.8)$M_2O$ : $Al_2O_3$ : $xSiO_2$ wherein R is an organic cation, M is an alkali metal cation and x is greater than 8, and is characterized by a specified X-ray powder diffraction pattern.

In a preferred synthesized form, zeolite ZSM-35 has a formula, in terms of mole ratios of oxides and in the anhydrous state, as follows:

(0.4 to 2.5)$R_2O$ : (0 to 0.6)$M_2O$ : $Al_2O_3$ : $ySiO_2$ wherein R is an organic nitrogen-containing cation, M is an alkali metal, especially sodium, and y is from greater than 8 to about 50.

In ZSM-35, as synthesized, R may be the organic cation derived from ethylenediamine, pyrrolidine, butanediamine or an N-methylpyridinium compound, such as the hydroxide, sulfate, nitrate or halide (e.g. bromide, chloride or iodide).

ZSM-38 is described in U.S. Pat. No. 4,046,859, the disclosure of which is incorporated herein by reference. This zeolite can be identified, in terms of mole ratios of oxides and in the anhydrous state, as follows:

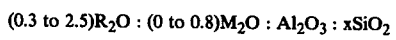
(0.3 to 2.5)$R_2O$ : (0 to 0.8)$M_2O$ : $Al_2O_3$ : $xSiO_2$ wherein R is an organic cation, M is an alkali metal cation and x is greater than 8, and is characterized by a specified X-ray powder diffraction pattern.

In a preferred synthesized form, zeolite ZSM-38 has a formula, in terms of mole ratios of oxides and in the anhydrous state, as follows:

(0.4 to 2.5)R$_2$O : (0 to 0.6)M$_2$O : Al$_2$O$_3$ : ySiO$_2$ wherein R is an organic nitrogen-containing cation derived from a 2-(hydroxyalkyl) trialkylammonium compound, wherein alkyl is methyl, ethyl or a combination thereof, M is an alkali metal, especially sodium, and y is from greater than 8 to about 50.

The above-identified zeolites possess definite distinguishing crystalline structures whose X-ray diffraction patterns show significant lines as indicated in the above incorporated references. The synthetic zeolites mentioned above may be prepared as indicated in the above incorporated references.

For convenience, the definite distinguishing crystalline structure of zeolite ZSM-35 exhibits an X-ray diffraction pattern showing substantially the significant lines set forth in Table 1, hereinafter presented. The definite distinguishing crystalline structure of zeolite ZSM-38 exhibits an X-ray diffraction pattern showing substantially the significant lines set forth in Table 2.

TABLE 1

| d(Å) | I/Io |
|---|---|
| 9.6 ± 0.20 | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium-Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak-Medium |
| 3.14 ± 0.06 | Weak-Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

TABLE 2

| d(Å) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 5.0 ± 0.10 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

The values of Tables 1 and 2 were determined by standard technique. The radiation was the K-alpha doublet of copper and a scintillation counter spectrometer with a strip chart pen recorder was used. The peak heights, I, and the positions as a function of 2 times theta, where theta is the Bragg angle, were read from the spectrometer chart. From these, the relative intensities, 100 I/Io, where Io is the intensity of the strongest line or peak, and d (obs.), the interplanar spacing in Angstrom units, corresponding to the recorded lines, were calculated. It should be understood that the data of Tables 1 and 2 are characteristic of all species of ZSM-35 and ZSM-38 compositions, respectively. Ion exchange of the sodium ion with cations reveals substantially the same pattern with some minor shifts in interplaner spacing and variation in relative intensity. Other minor variations can occur depending on the silicon to aluminum ratio of the particular sample, as well as if it has previously been subjected to thermal treatment.

The zeolites for use as the catalyst in the present process may be used as manufactured, as the product of thermal treatment thereof at a temperature of from about 100° C. to about 800° C., as ion exchanged with one or more cations selected from the group consisting of hydrogen and metals from Groups IIA, IIIA, IVA, IB, IIB, IIIB, IVB, VIB and VIII of the Periodic Table of Elements and rare earth metals. A hydrogen precursor, such as an ammonium compound, may be used as the source of hydrogen ions and of the replacing metal cations particular preference is given to Mn, Ca, Mg, Zn, Cd, Pt, Pd, Ni, Co, Ti, Sn and Fe.

Typical ion exchange technique would be to contact the zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperture ranging from 50° C. to about 300° C. and thereafter may be calcined in air or other inert gas at from about 200° C. to a temperature below the zeolite decomposition temperature, preferably about 900° C., for periods of time ranging from 1 to 48 hours or more to produce a catalytically-active thermal decomposition product thereof.

Regardless of the replacing or additional cations in the zeolites for use herein, the spacial arrangement of the aluminum, silicon and oxygen atoms which form the basic crystal lattices of the zeolite remains essentially unchanged by the described replacement of alkali metal as determined by taking an X-ray powder diffraction pattern of the ion-exchanged material.

It is desired to incorporate the zeolite for use herein with another material resistant to the témperatures and other conditions employed in the present process. Such matrix materials include inactive materials and synthetic or naturally occurring zeolites as well as inorganic materials such as clays, silica and/or metal oxides. The latter may be either naturally occurring zeolites as well as inorganic materials such as clays, silica and/or metal oxides. The latter may be either naturally occurring or in the form of gelatinous precipitates, sols or gels including mixtures of silica and metal oxides. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the zeolite for use herein include the montmorillonite and kaolin families which include the sub-bentonites and the kaolins commonly known as Dixie, McNamee, Georgia and Florida clays or others in which the main mineral constituents is halloysite, kaolinite, dickite, nacrite or anauxite. Such clays can be used in the raw state as originally mined or initially subjected to calcination, acid treatment or chemical modification.

In addition to the foregoing materials, the zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided zeolite and inorganic oxide gel matrix vary widely with the crystalline aluminosilicate content ranging from about 1 to about 99 percent by weight and more usually in the range of about 2 to about 80 percent by weight of the composite.

The zeolites for use herein have an exceptionally high degree of thermal stability thereby rendering them particularly effective for use in processes involving elevated temperatures. In this connection, ZSM-35 and ZSM-38 appear to be two of the most stable zeolites known to date. However, it has been found that the process of this invention may be carried out at reactor bed temperatures not in excess of about 650° C. At reactor bed temperatures substantially above 650° C., products of the present process may undergo degradation resulting in the loss of desired products and reactants. Undesirable residues may be formed from the degradation reactions. In addition, olefins used as alkylating agents may polymerize with themselves or other reactants to form resinous compounds within the reaction zone. These resinous compounds together with the degradation products may lead to the formation of coke-like deposits on the active surfaces of the catalyst. As a result, these deposits rapidly destroy the high activity of the catalyst and greatly shorten its effective life. Such undesirable effects are limited under the conditions and with the catalyst employed in the present process.

Of particular importance for a practical alkylation or transalkylation process is that the catalyst has a long useful life and does not deactivate rapidly. In this respect it has been found that the catalyst for use herein has an extraordinary resistance to deactivation not found by prior art catalysts such as faujasite or mordenite zeolite catalysts. With the latter catalysts, many undesirable side reactions always accompany the catalytic alkylation or transalkylation of aromatic hydrocarbons.

While the exact reason for this unusual behavior is not fully established, it is believed to result from the specific structure and dimensions of the pores of ZSM-35 and ZSM-38, which have smaller cross-sectional dimensions than those of the previously mentioned zeolites (e.g. faujasite and mordenite) but are still large enough to admit aromatic molecules. ZSM-35 and ZSM-38 differ in this regard from the catalytically inactive small pore zeolites A and erionite. In addition, the high $SiO_2/Al_2O_3$ ratio of ZSM-35 and ZSM-38 also is believed to be a contributing factor to its long catalyst life.

The aluminosilicate prepared for use in the instant invention may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

Exemplary of the hydrocarbons which may be alkylated or transalkylated by the process of this invention, depending upon whether an alkylating agent or a transalkylating agent is employed, are aromatic compounds such as benzene, naphthalenes, anthracenes, and the like and substituted derivatives thereof; and alkyl substituted aromatics, e.g. toluene, xylene, and homologs thereof. In general, non-polar substituent groups may be attached to the nucleus of the aromatic ring including, by way of non-limiting example:

Alkyl ($-C_nH_{(2n+1)}$), such as methyl, ethyl, propyl and tert-butyl;

Cycloalkyl ($-C_nH_{(2n-1)}$), such as cyclopentyl and cyclohexyl; and

Aryl, such as phenyl and naphthyl.

In accordance with this invention and when alkylation is to be accomplished, the preferred alkylating agents are olefins such as, for example, ethylene, propylene, butene, decene, dodecene, as well as formaldehyde, alkyl halides and alcohols; the alkyl portion thereof having from 1 to 24 carbon atoms. Numerous other acyclic compounds having at least one reactive alkyl radical may be utilized as alkylating agents.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene and ethyltoluene.

It is interesting to note in regard to the utility of the ZSM-35 zeolite as the catalyst for use herein that it has a one-dimensional channel system of about 6 Angstrom Units maximum, that is about 1 Angstrom Unit smaller than that of ZSM-5 (U.S. Pat. No. 3,702,886) and considerably smaller than those of many other zeolites known in the art to have catalytic activity for alkylation and transalkylation reactions. In view of this, the excellent utility of the ZSM-35 zeolite with respect to such reactions is unexpected.

Operating conditions employed in the process of the present invention are dependent, at least in part, on the specific alkylation or transalkylation reaction being effected. Such conditions as temperature, pressure, space velocity and molar ratio of the reactants and the presence of inert diluents will have important affects on the process.

When alkylation is the process conducted according to this invention and the alkylating agent is an olefin, the temperature of the reaction is preferably within the range of about 37° C. to about 510° C., with a particularly preferred temperature range of about 200° C. to about 485° C. When the alkylating agent is an alcohol, the preferred reaction temperature is within the range of about 200° C. to about 650° C., with a particularly preferred temperature range of about 370° C. to about 607° C.

When transalkylation is the process conducted according to the invention, the reaction temperature is preferably within the range of about 340° C., to about 595° C., with a particularly preferred temperature range of about 398° C. to about 510° C.

Preferred reaction pressure in either alkylation or transalkylation according to the present invention is from about 25 psig to about 800 psig. In any case, the preferred weight hourly space velocity is within the range of about 1 to about 20.

The process of this invention is conducted such that alkylation or transalkylation of an aromatic hydrocarbon compound, exemplified by benzene, with an alkylating agent, such as an olefin, exemplified by ethylene, or a transalkylating agent, such as a polyalkylaromatic hydrocarbon, exemplified by 1,3,5-trimethylbenzene, is carried out by contact in a reaction zone, such as, for example, a fixed bed of catalyst, under alkylation or transalkylation effective conditions, said catalyst being characterized as comprising an above-defined ZSM-35 and/or ZSM-38 zeolite.

For alkylation, the alkylatable aromatic compound and alkylating agent are desirably fed to a first stage at an appropriate mole ratio of one to the other. The feed to such first stage is heated. After some reaction takes place, such as, for example, when about 80 percent of the alkylating agent is consumed, the effluent of the first stage is cooled to remove heat of reaction and more alkylating agent is added (second stage) to maintain the mole ratio of aromatic compound to alkylating agent within the range established for the first stage. A plurality of reaction stages are possible for the process of this invention. It is generally desirable to provide cooling between reactor stages.

Considering, for example, alkylation of benzene with ethylene, the first stage mole ratio of benzene to ethylene may be in the range of about 1:3 to about 20:1. The first stage feed is heated to a reactor inlet temperature within the range of about 37° C. to about 650° C. at a pressure within the range of about atmospheric to about 3000 psig. Preferred inlet temperatures fall within the range of about 37° C. to about 510° C. and preferred pressures fall within the range of about 25 psig to about 800 psig. The repeating of reaction staging is carried out while maintaining an overall aromatic hydrocarbon, e.g., benzene, to alkylating agent, e.g., ethylene, mole ratio of about 1:3 to about 20:1, with a preferred range of about 1:2 to about 16:1. As the reaction proceeds through the stages, the aromatic to alkylating agent mole ratio increases.

In conducting a transalkylation reaction in accordance with the present invention, a single stage reactor is usually sufficient. Suitable mole ratios of aromatic hydrocarbon to transalkylating agent range from 1:3 to 20:1, and preferably range from 1:2 to 5:1. Preferred reaction pressures in this case fall within the range of about 25 psig to about 800 psig.

It is noted that disproportionation is a special case of transalkylation in which the alkylatable aromatic hydrocarbon and the transalkylating agent is the same compound, for example when toluene serves as the donor and acceptor of a transferred methyl group to produce benzene and xylene. It should be understood that the term transalkylation as used herein includes the special case of disproportionation.

It is also noted that extremely high total feed space velocities are possible in the process of this invention, i.e. up to 1000 pounds total feed/hour-pound crystalline aluminosilicate. An important factor in the present process is, however, the weight hourly space velocity (WHSV) of the alkylating agent or transalkylating agent. The alkylating agent or transalkylating agent WHSV to each of any alkylation or transalkylation reactor stages is maintained between about 1 and about 10 pounds agent/hour-pound crystalline aluminosilicate. The most desirable alkylating agent or transalkylating agent WHSV is within the range of about 2 to about 6 pounds agent/hour-pound crystalline aluminosilicate. When the WHSV is maintained within the above limits, an economical cycle between regenerations of catalyst exists.

The process, of course, can be conducted with either a fixed or fluidized catalyst bed, with attendant benefits in either circumstance readily attainable.

The following examples will serve to illustrate the process of the invention, without unduly limiting same.

EXAMPLE 1

Illustrating preparation of synthetic zeolite ZSM-35, a first solution comprising 33.0 grams sodium aluminate (41.8% $Al_2O_3$, 31.6% $Na_2O$ and 24.9% $H_2O$), 870 grams $H_2O$ and 3.4 grams NaOH (50% solution with water) was prepared. The organic material pyrrolidine was added to the first solution in 182.0 gram quantity to form a second solution. Thereupon 824 grams colloidal silica (29.5% $SiO_2$ and 70.5% $H_2O$) was added to the second solution and mixed until a homogeneous gel was formed. The gel was composed of the following components in mole ratios:

| | |
|---|---|
| $\dfrac{R^+}{R^+ + M^+}$ | 0.87, wherein M is sodium and $R^+$ is the pyrrolidine ion. |
| $\dfrac{OH^-}{SiO_2}$ | 0.097 (Not including any contribution of $OH^-$ from pyrollidine) |
| $\dfrac{H_2O}{OH^-}$ | 202 (Not including any contribution of $OH^-$ from pyrrolidine) |
| $\dfrac{SiO_2}{Al_2O_3}$ | 29.0 |

The mixture was maintained at 135° C. for 17 days, during which time crystallization was complete. The product crystals were filtered out of solution and water washed for approximately 16 hours on continuous wash line.

X-ray analysis of the crystalline product proved the crystals to have a diffraction pattern as shown in Table 1.

Chemical analysis of the crystalline product led to the following compositional figures:

| Composition | Mole Ratio on Al$_2$O$_3$ Basis |
|---|---|
| N$_2$O | 1.23 |
| Na$_2$O | 0.08 |
| SiO$_2$ | 29.00 |

Physical analysis of the crystalline product of Example 1 calcined 16 hours at 538° C. showed it to have a surface area of 349 m$^2$/g and adsorption tests produced the following results:

| Adsorption | Wt. % |
|---|---|
| Cyclohexane | 2.1 |
| n-Hexane | 8.2 |
| Water | 11.0 |

EXAMPLE 2

Illustrating a preparation of zeolite ZSM-38, a first solution was prepared comprising 34.4g sodium silicate (28.8% SiO$_2$, 8.9% Na$_2$O and 62.2% H$_2$O), 2.4g sodium aluminate (44.7% Al$_2$O$_3$, 31.3% Na$_2$O and 24.0% H$_2$O), 9.7g NaOH and 76.4g water. A second solution was prepared by first mixing 23.74g Al$_2$(SO$_4$)$_3$ 14 H$_2$O, 12.5g H$_2$SO$_4$ and 75.0g water and then adding to that mixture 135.0g of the sodium silicate. At this point, the second solution was added to the first solution to provide a gel which was mixed until homogeneous and aged at 99° C. for 1-2 hours. The solid which formed was filtered out and the filtrate was discarded. A third solution, made up of 18.72g of 2-(hydroxyethyl) trimethylammonium chloride, 10.0g of 10% NaOH solution and 20.0g water, was then added to the above solid and the resulting mixture was mixed until homogeneous and crystallized (99° C. for 83 days).

The crystallization mixture was comprised of the following components in mole ratios:

| | |
|---|---|
| $\dfrac{R^+}{R^+ + M^+}$ | 0.31, wherein M is sodium and R is [(CH$_3$)$_3$—N—CH$_2$CH$_2$OH] |
| $\dfrac{OH^-}{SiO_2}$ | 0.36 |
| $\dfrac{H_2O}{OH^-}$ | 52.2 |
| $\dfrac{SiO_2}{Al_2O_3}$ | 16.4 |

The crystalline product was filter separated, water washed and X-ray analyzed. The X-ray analysis showed the crystalline product of this example to have the diffraction pattern shown below:

| X-RAY DIFFRACTION PATTERN OF ZSM-38 OF EXAMPLE 2 | | |
|---|---|---|
| 2 Times Theta | d(A) | I/Io |
| 9.02 | 9.80 | 45 |
| 9.70 | 9.12 | 29 |
| 11.10 | 7.97 | 2 |
| 12.50 | 7.08 | 34 |
| 13.25 | 6.68 | 34 |
| 14.70 | 6.03 | 15 |
| 15.20 | 5.83 | 11 |
| 17.75 | 5.00 | 13 |
| 18.77 | 4.73 | 11 |
| 20.33 | 4.37 | 7 |
| 21.00 | 4.23 | 5 |
| 22.15 | 4.01 | 82 |
| 23.35 | 3.81 | 68 |
| 24.10 | 3.69 | 23 |
| 24.97 | 3.57 | 100 |
| 25.40 | 3.51 | 100 |
| 26.70 | 3.34 | 26 |
| 28.17 | 3.17 | 48 |
| 28.97 | 3.08 | 24 |
| 29.76 | 3.00 | 17 |
| 30.60 | 2.921 | 29 |
| 32.75 | 2.734 | 5 |
| 33.73 | 2.657 | 11 |
| 34.55 | 2.596 | 6 |
| 36.00 | 2.495 | 7 |
| 36.90 | 2.436 | 3 |
| 37.87 | 2,376 | 4 |
| 38.60 | 2.332 | 4 |
| 39.70 | 2.270 | 2 |
| 42.50 | 2.127 | 4 |
| 43.80 | 2.067 | 2 |
| 44.50 | 2.036 | 7 |

Chemical analysis of the product of this example provided the following compositional figures:

| Composition | Wt. % | Mole Ratio on Al$_2$O$_3$ Basis |
|---|---|---|
| N | 1.35 | — |
| Na | 2.60 | — |
| Al$_2$O$_3$ | 12.60 | 1 |
| SiO$_2$ | 83.5 | 11.85 |
| N$_2$O | — | 0.53 |
| Na$_2$O | — | 0.48 |
| H$_2$O | — | 5.28 |

Physical analysis of the product of this example indicated that the surface area of the crystals after calcination at 538° C. for 16 hours was 372 m$^2$/g. Adsorption tests provided the following data:

| Adsorption | Wt. % |
|---|---|
| Cyclohexane | 5.2 |
| n-Hexane | 7.2 |
| Water | 11.2 |

EXAMPLE 3

In yet another illustration of the preparation of ZSM-38, a first solution was prepared comprising 103.2 grams sodium silicate (as defined in Example 2), 7.2 grams sodium aluminate (as defined in Example 2), 29.1 grams sodium hydroxide and 229.2 grams water. A second solution was prepared by first mixing 71.22 grams Al$_2$(SO$_4$)$_3$.14H$_2$O, 37.5 grams H$_2$SO$_4$ and 225 grams water and then adding to that mixture 405 grams of the sodium silicate. The second solution was then added to the first solution and the resultant gel was mixed until homogeneous and aged at 99° C. for 1-2 hours. The solid which formed was then filtered out of solution and the filtrate was discarded. A third solution, made up of 56.2 grams 2-(hydroxyethyl) trimethylammonium chloride, 30.0 grams of 10% sodium hydroxide solution and 60.0 grams water, was then added to the above solid and the resulting mixture was mixed until homogeneous and crystallized (99° C. for 70 days).

The crystallization mixture was comprised of the following components in moles or measurements in mole ratios:

| | |
|---|---|
| $\dfrac{R^+}{R^+ + M^+}$ | 0.31, wherein M and R are as defined in Example 2 |
| $\dfrac{OH^-}{SiO_2}$ | 0.35 |
| $\dfrac{H_2O}{OH^-}$ | 52.2 |
| $\dfrac{SiO_2}{Al_2O_3}$ | 16.1 |

The crystalline product was filter separated, water washed and X-ray analyzed. The X-ray analysis showed the crystalline product of Example 3 to have the diffraction pattern of Table 2.

Chemical analysis of the product of Example 3 provided the following compositional figures:

| Composition | Wt. % | Mole Ratio on $Al_2O_3$ Basis |
|---|---|---|
| N | 1.41 | — |
| Na | 2.20 | — |
| $Al_2O_3$ | 11.6 | 1.0 |
| $SiO_2$ | 87.5 | 12.83 |
| $N_2O$ | — | 0.77 |
| $Na_2O$ | — | 0.42 |
| $H_2O$ | — | 6.20 |

Physical analysis of the product of Example 3 calcined 16 hours at 538° C. indicated that the surface area of the crystals was 403 m²/g. Adsorption tests provided the following data:

| Adsorption | Wt. % |
|---|---|
| Cyclohexane | 7.1 |
| n-Hexane | 7.1 |
| Water | 13.4 |

EXAMPLE 4

Over a fixed bed of catalyst as prepared in Example 1 a feed of toluene was contacted with the alkylating agent methyl alcohol in the mole ratio of toluene to methyl alcohol of 2:1. The reactor inlet temperature was 232° C. and the reactor pressure was maintained at 400 psig. The total feed weight hourly space velocity was 8 and the time of reaction was 4.9 hours. Table 3 lists the composition of the liquid product in weight percent, conversion in weight percent and selectivity calculated as (weight percent xylene/weight percent conversion) × 100%.

EXAMPLE 5

The same catalyst from Example 4 was then tested (without regeneration) as in Example 4 for 14.7 hours with only the weight hourly space velocity changed to 2. The results of this example also appear in Table 3.

EXAMPLE 6

The same catalyst from Example 5 was then tested (without regeneration) as in Example 4 for 1.9 hours with the temperature raised to 288° C. and the weight hourly space velocity maintained at 8. The results of this example also appear in Table 3.

EXAMPLE 7

The catalyst from Example 6 was then tested (without regeneration) as in Example 4 for 1.7 hours with only the temperature changed to 343° C. The results of this example also appear in Table 3.

EXAMPLE 8

The catalyst from Example 7 was then tested (without regeneration) as in Example 4 for 1.6 hours with only the temperature changed to 399° C. The results of this example also appear in Table 3.

EXAMPLE 9

The catalyst from Example 8 was then tested (without regeneration) as in Example 8 for 2.7 hours with only the weight hourly space velocity changed to 4. The results of this example also appear in Table 3.

EXAMPLE 10

The catalyst from Example 9 was then tested (without regeneration) as in Example 6 for 16.3 hours with only the weight hourly space velocity changed to 2. The results of this example also appear in Table 3.

EXAMPLE 11

The catalyst from Example 10 was then tested (without regeneration) as in Example 7 for 5.9 hours with the reaction pressure maintained at 1 atmosphere and the weight hourly space velocity changed to 4. The results of this example also appear in Table 3.

EXAMPLE 12

The catalyst from Example 11 was then tested (without regeneration) as in Example 7 for 47.9 hours with only the weight hourly space velocity changed to 4. The results of this example also appear in Table 3.

TABLE 3

ALKYLATION OF TOLUENE WITH METHANOL OVER ZSM-35

| Example | Product Analysis (Weight Percent) | | | | | | Weight percent[a] Conversion | Selectivity |
|---|---|---|---|---|---|---|---|---|
| | Benzene | Toluene | Xylenes | p-Xylene | m-Xylene | o-Xylene | $C_9$+ | |
| 4 | 0 | 99.60 | 0.38 | 0.20 | | 0.18 | 0 | 0.4 | 95[b] |
| 5 | 0 | 99.00 | 0.91 | 0.21 | 0.21 | 0.45 | 0 | 1.0 | 91[b] |
| 6 | 0.01 | 93.06 | 5.97 | 1.54 | 1.35 | 3.08 | 0.86 | 6.94 | 86.0 |
| 7 | 0.24 | 75.72 | 16.20 | 3.79 | 8.75 | 3.66 | 7.64 | 24.3 | 66.7 |
| 8 | 1.33 | 65.97 | 21.36 | 5.22 | 11.31 | 4.83 | 10.93 | 34.0 | 62.8 |
| 9 | 1.73 | 67.31 | 20.70 | 4.99 | 11.22 | 4.50 | 9.85 | 32.7 | 63.3 |
| 10 | 0.04 | 95.27 | 3.81 | | 1.94 | 1.87 | 0.78 | 4.7 | 81.1 |
| 11 | 0.02 | 84.54 | 12.48 | 3.31 | 3.62 | 5.56 | 2.82 | 15.5 | 80.5 |
| 12 | 0.06 | 77.71 | 14.32 | | 6.83 | 7.49 | 7.19 | 22.3 | 64.2 |

[a]Conversion of toluene; maximum conversion possible is 50%
[b]Selectivity in mole percent xylene.

EXAMPLE 13

A 1.0 cc portion (0.63 gram) of the product crystalline zeolite ZSM-35 of Example 1 was placed in a glass reactor and heated from 24° C. to 538° C. in flowing air (100 cc/minute) and held at 538° C. for one hour. An equimolar mixture of toluene and 1,2,4-trimethylbenzene was then passed over the catalyst at 510° C. and atmospheric pressure. The weight hourly space velocity was maintained at 1 hr$^{-1}$. The results of this example appear in Table 4, hereinafter presented.

EXAMPLE 14

The experiment outlined in Example 13 was repeated, except that the temperature was 455° C. and the weight hourly space velocity was maintained at 4 hr$^{-1}$. The results of this example are also listed in Table 4.

TABLE 4
TRANSALKYLATION OVER ZSM-35

| Example No. Product Analysis (Wt. %) | Feed | 13 | 14 |
|---|---|---|---|
| Benzene | | 5.0 | 1.3 |
| Toluene | 43.4 | 32.7 | 38.1 |
| p,m-Xylene | | 22.7 | 10.8 |
| o-Xylene | | 6.8 | 3.1 |
| Total Xylene | | 29.5 | 13.9 |
| TMB[a] | 56.6 | 29.3 | 45.5 |
| Other C$_9$+ | | 3.0 | 1.2 |
| Conversion[b] | | 71.5 | 33.4 |

[a]1,2,4-Trimethylbenzene
[b]Conversion to xylenes (percent of equilibrium).

EXAMPLE 15

Propylene was bubbled through a 68° C. benzene solution containing a quantity of the ZSM-35 zeolite prepared in Example 1 in the ratio of 10 grams of benzene per gram of zeolite catalyst. Cumene was produced at the hourly rate of 14 grams per 100 grams of zeolite ZSM-35 catalyst.

EXAMPLE 16

In order to compare the aging properties of the catalyst for use in the present process with the same properties of a commercially available catalyst used in the art for alkylation or transalkylation, a quantity of Zeolon 100H, a commercially available form of synthetic hydrogen-mordenite, was pretreated by heating through the range of 21° C. to 538° C. over a 1.5 hour period followed by 1.0 hour at 538° C. The heating was accomplished in the presence of dry air flowing at the rate of 100 cc/minute.

A quantity of the ZSM-35 zeolite as prepared in Example 1 and an equal quantity of the pretreated commercial catalyst were placed in identical reactors, each held at a temperature of 427° C. while an equimolar mixture of toluene and 1,2,4-trimethylbenzene were passed therethrough at a weight hourly space velocity of 4hr$^{-1}$. The results of this experiment are shown in Table 5. It is noted that conversion to xylenes with the commercial catalyst is quite high at the start of the experiment, but almost nil (0.8%) after 2.5 hours on stream. The catalyst for use in the present process was still providing a 19.3% conversion after 2.5 hours of the test.

TABLE 5

| | ZSM-35 | Commercial Catalyst | ZSM-35 | Commercial Catalyst |
|---|---|---|---|---|
| Time on stream (hours) | 0.13 | 0.17 | 2.5 | 2.5 |
| Product Analysis (wt.%) | | | | |
| Benzene | 1.38 | 2.83 | 0.58 | 0 |
| Toluene | 36.77 | 28.68 | 39.55 | 43.91 |
| Xylene | 13.00 | 29.72 | 7.99 | 0.31 |
| TMB[a] | 47.61 | 35.53 | 51.08 | 55.67 |
| Other C$_9$+ | 1.17 | 3.08 | 0.74 | 0.09 |
| Conversion[b] | 31.50 | 72.00 | 19.30 | 0.8 |

[a]1,2,4-Trimethylbenzene
[b]Conversion to xylenes (percent of equilibrium).

EXAMPLE 17

A 100 gram quantity of naturally occurring ferrierite ore was made into the hydrogen cation-containing form (H-ferrierite) by ammonium exchanging said ore at 25° C., with stirring, as follows:

(1) contacting the ore with 2.0 liters of 0.2 N NH$_4$NO$_3$ solution for 20 hours, filtering and washing with distilled water, then (2) contacting a second time with 2.0 liters of 4.0 N NH$_4$NO$_3$ solution for 69 hours, filtering and washing with distilled water, then (3) contacting a third time with 2.0 liters of 4.0 N NH$_4$NO$_3$ solution for 42 hours, filtering and washing with distilled water; and then (4) contacting a fourth time with 2.0 liters of 0.01 N NH$_4$NO$_3$ solution for 22 hours, filtering, washing with distilled water and drying.

The treated ferrierite ore was then calcined in air for 10 hours at 538° C.

EXAMPLE 18

A 1.0 cc portion of the product crystalline zeolite ZSM-35 of Example 1 was placed in a glass reactor and heated from 24° C. to 538° C. in flowing air (100 cc/minute) and held at 538° C. for one hour. An equimolar mixture of toluene and 1,2,4-trimethylbenzene was then passed over the catalyst at 427° C. and atmospheric pressure. The weight hourly space velocity was maintained at 4 hr$^{-1}$. The results of this experiment appear in Table 6, hereinafter presented.

EXAMPLE 19

The experiment of Example 18 was repeated under identical conditions with the exception that the H-ferrierite prepared in Example 17 was used as catalyst in place of the ZSM-35. The results of this experiment appear in Table 6, below. It is apparent from comparison of the data obtained from the experiments of Examples 18 and 19 that a catalyst material of naturally occurring ferrierite is considerably less active than the synthetic zeolite for use in the present process.

TABLE 6
TRANSALKYLATION OVER ZSM-35 AND ACTIVATED NATURAL FERRIERITE

| Example No. | Feed | 18 | 19 |
|---|---|---|---|
| Product Analysis (Wt. %) | | | |

TABLE 6-continued
TRANSALKYLATION OVER ZSM-35 AND ACTIVATED NATURAL FERRIERITE

| Example No. | Feed | 18 | 19 |
|---|---|---|---|
| Benzene | | 0.8 | 0 |
| Toluene | 43.4 | 39.6 | 41.4 |
| Total Xylenes | | 9.6 | 1.5 |
| TMB[a] | 56.6 | 49.0 | 56.5 |
| Other C$_9$+ | | 0.9 | 0.6 |
| Conversion[b] | | 23.3 | 3.6 |

[a]1,2,4-Trimethylbenzene.
[b]Conversion to xylenes (percent of equilibrium).

EXAMPLE 20

The experiment of Example 18 was repeated under identical conditions with the exception that the ZSM-35 catalyst used in Example 18 was replaced with a 1.0cc portion of the product crystalline zeolite ZSM-38 of Example 3. Transalkylation occurred to produce predominently xylenes and in addition a small amount of benzene and C$_9$+ material. Conversion in this experiment to xylenes was 57 weight percent (of equilibrium). When this result is compared with the 3.6 weight percent conversion obtained in Example 19, it is readily observed that a zeolite ZSM-38 can provide up to 1480 percent more transalkylation of aromatics than an activated natural ferrierite.

EXAMPLE 21

In this experiment, propylene was bubbled through a 68° C. benzene solution containing a quantity of the ZSM-38 zeolite prepared in Example 3 in the ratio of 10 grams of benzene per gram of zeolite catalyst. Cumene was produced at the hourly rate of 95 grams per 100 grams of catalyst.

EXAMPLE 22

In a further synthesis of zeolite ZSM-35, two solutions were employed. The first solution was prepared with 2.5 grams Al$_2$(SO$_4$)$_3$.16H$_2$O, 1.7 grams concentrated sulfuric acid, and 35.3 grams of water to which 1.4 grams of the organic liquid 1,4-butanediamine (BDN) was added. A second solution was prepared in a teflon bottle with 25.0 grams of sodium silicate (27.8% SiO$_2$, 8.42% Na$_2$O, 63.78% H$_2$O) and 31.3 grams of water. The first solution was added to the second solution and mixed until a homogeneous gel formed. The mixture was maintained at 140° C., without stirring, for 3 days, during which time crystallization was complete.

The crystallization reaction mixture was comprised of the following components in mole ratios:

| | | |
|---|---|---|
| $\dfrac{SiO_2}{Al_2O_3}$ | 30 | |
| $\dfrac{H_2O}{SiO_2}$ | 40 | |
| $\dfrac{OH^-}{SiO_2}$ | 0 | (Not including any contribution of OH$^-$ from BDN) |
| $\dfrac{Na^+}{SiO_2}$ | 0.59 | |
| $\dfrac{BDN}{SiO_2}$ | 0.14 | |

These figures were determined assuming that Al$_2$O$_3$ consumes two moles of OH$^-$ in its conversion to framework AlO$_2$$^-$. Also, moles of OH$^-$ are defined as moles of OH$^-$ added less any moles of mineral acid (H$^+$) added to the mixture. The pH of the reaction mixture was greater than 7.

The product crystals were filtered out of solution and washed with water. They were then heated in water, with stirring, for 20 minutes and subsequently filtered, washed with water, and dried.

X-ray analysis of the crystalline product proved the crystals to have a diffraction pattern as shown in Table 1.

Chemical analysis of the crystalline product led to the following compositional figures:

| Composition | Mole Ratio on Al$_2$O$_3$ Basis |
|---|---|
| N$_2$O | 1.01 |
| Na$_2$O | 0.18 |
| SiO$_2$ | 26.4 |

EXAMPLE 23

Another sample of zeolite ZSM-35 was synthesized in a manner similar to that in Example 22. A first solution was prepared with 0.7 gram of sodium aluminate (40% Al$_2$O$_3$, 33% Na$_2$O, 27% H$_2$O), 1.92 grams NaOH, 6.1 grams N-methylpyridinium iodide (MPYI) and 57.9 grams of water. Into a teflon bottle was measured 21.4 grams colloidal silica (30% SiO$_2$, 70% H$_2$O). The first solution was then added to the colloidal silica and mixed until a homogeneous gel was produced. The pH of the mixture was greater than 7. The mixture composition, calculated as described in Example 22, was as follows:

| | |
|---|---|
| $\dfrac{SiO_2}{Al_2O_3}$ | 39 |
| $\dfrac{H_2O}{SiO_2}$ | 39 |
| $\dfrac{OH^-}{SiO_2}$ | 0.52 (Not including any contribution of OH$^-$ from MPYI) |
| $\dfrac{Na^+}{SiO_2}$ | 0.52 |
| $\dfrac{MPY}{SiO_2}$ | 0.26 |

The reaction mixture was maintained at 150° C., without stirring, for 7 days, during which time crystallization was complete. The product crystals were filtered out of solution and washed with water and treated as described in Example 22 prior to final drying. X-ray analysis of the crystalline product produced a diffraction pattern as indicated in Table 1.

Chemical analysis of the crystalline product gave the following compositional figures:

| Composition | Mole Ratio on Al$_2$O$_3$ Basis |
|---|---|
| N$_2$O | 1.56 |
| Na$_2$O | 0.33 |
| SiO$_2$ | 34.1 |

EXAMPLE 24

A 6.2 gram quantity of the product zeolite ZSM-35 of Example 23 was contacted twice with 2M NH$_4$NO$_3$ solution, each contacting at reflux for one hour; washed with hot water and then calcined in air for 10 hours at 538° C.

A 1.0 cc portion (0.65 gram) of the exchanged zeolite was placed in a glass reactor and heated from 24° C. to 538° C. in flowing air (100 cc/minute) and held at 538° C. for one hour. An equimolar mixture of toluene and 1,2,4-trimethylbenzene was then passed over the catalyst at 427° C., one atmosphere pressure and a weight hourly space velocity of 4 hr$^{-1}$. A sample collected after 0.13 hour on stream contained 4.8 wt. % xylenes which is 12% of equilibrium conversion.

EXAMPLE 25

A 1.95 gram quantity of the product zeolite ZSM-35 of Example 22 was calcined in air for 10 hours at 538° C., contacted twice with 100 ml of 0.5 N HN$_4$Cl solution, each contacting at 24° C., the first contacting for 4 hours, the second contacting for 16 hours; washed with water; air dried and then calcined in air for 10 hours at 538° C.

A 1.0 cc portion (0.55 gram) of the exchanged zeolite was placed in a glass reactor and heated from 24° C. to 538° C. in flowing air (100 cc/minute) and held at 538° C. for one hour. An equimolar mixture of toluene and 1,2,4-trimethylbenzene was then passed over the catalyst at 427° C., one atmosphere pressure and a weight hourly space velocity of 4 hr$^{-1}$. A sample collected after 0.13 hour on stream contained 7.0 wt. % xylenes which is 17% of equilibrium conversion.

EXAMPLE 26

In a 250 ml flask fitted with a stirrer and a reflux condenser is placed 100 grams of benzene and 10 grams of HZSM-35 prepared as in Example 25. The flask is heated by an external electrical heating mantle until a thermometer placed inside shows a temperature of about 68° C. While stirring the catalyst suspension, propylene is bubbled through the solution at a rate of 60 ml of propylene per minute. After 5 hours, the liquid contents is separated from the catalyst by filtration. Analysis of the liquid by gas chromatography shows that isopropylbenzene (cumene) has been formed in an amount of about 5 grams by the alkylation of benzene.

EXAMPLE 27

Example 26 is repeated except that 12 grams of HZSM-35 prepared as in Example 24 is used and the duration of the experiment is 8 hours. During that time, about 6.7 grams of cumene is produced.

EXAMPLE 28

Three grams of exchanged zeolite prepared as in Example 25 is placed into a stainless steel vertical flow reactor and heated to 427° C. in a stream of helium. Benzene, at a rate of 45 grams per hour, is passed over the zeolite, together with ethylene at a ratio of 1 mole of ethylene per 8 moles of benzene, at a total pressure of 400 psig. The reactor effluent contains ethylbenzene and smaller amounts of diethylbenzene, formed by alkylation of benzene, in a yield exceeding 50% based on the ethylene.

EXAMPLE 29

Example 28 is repeated except that toluene is used as one of the feeds instead of benzene. The reactor effluent contains o-, m-, and p-ethyltoluene formed by alkylation of toluene in a selectivity exceeding 90%, and small amounts of benzene and xylenes, formed by transalkylation (disproportionation) of toluene.

It will be noted from the examples of this invention that the alkylation or transalkylation of aromatic hydrocarbon compounds by contacting with the zeolite ZSM-35 and/or ZSM-38 catalysts provides substantial benefits over a similar process with other catalysts known in the art for alkylation or transalkylation. For example, and possibly the most important fact, zeolites ZSM-35 and ZSM-38 exhibit markedly improved aging properties. Instead of cycle periods of a few hours as has been the practice of the prior art, a cycle of days or weeks is possible.

It will be appreciated that the examples set forth above are merely illustrative and that aromatic hydrocarbons including aromatic hydrocarbons containing a non-polar substituent, may be alkylated or transalkylated in accordance with the present invention.

It will also be appreciated that the operating conditions for the alkylation or transalkylation reactions in accordance with the process of this invention, as exemplified in the foregoing examples, may be varied within the limits specified and that various modifications and alterations may be made in the process of this invention without departing from the spirit and scope thereof.

What is claimed is:

1. A process for effecting alkylation of an aromatic hydrocarbon charge selected from the group consisting of aromatic hydrocarbons and aromatic hydrocarbons containing a non-polar substituent which comprises contacting said hydrocarbon charge with an alkylating agent under conditions effective for accomplishing said alkylation including a reactor inlet temperature between about 37° C. and about 650° C., a reactor pressure between atmospheric and about 3000 psig, a mole ratio of of hydrocarbon charge to alkylating agent in the approximate range of 1:3 to 20:1 and a weight hourly space velocity between about 0.5 hr$^{-1}$ and 1000 hr$^{-1}$ in the pressure presence of a catalyst comprising a crystalline aluminosilicate zeolite or a product of thermal treatment thereof at a temperature of from about 100° C. to about 800° C., said zeolite being selected from the group consisting of ZSM-35, ZSM-38 and a combination thereof.

2. A process for effecting transalkylation of an aromatic hydrocarbon charge selected from the group consisting of aromatic hydrocarbons and aromatic hydrocarbons containing a non-polar substituent which comprises contacting said hydrocarbon charge with a transalkylating agent under conditions effective for accomplishing said transalkylation including a reactor inlet temperature between about 37° C. and about 650° C., a reactor pressure between atmospheric and about 3000 psig, a mole ratio of hydrocarbon charge to transalkylating agent in the approximate range of 1:3 to 20:1 and a weight hourly space velocity between about 0.5 hr$^{-1}$ and 1000 hr$^{-1}$ in the presence of a catalyst comprising a crystalline aluminosilicate zeolite or a product of thermal treatment thereof at a temperature of from about 100° C. to about 800° C., said zeolite being selected from the group consisting of ZSM-35, ZSM-38 and a combination thereof.

3. The process of claim 1 wherein the alkylating agent is an olefin.

4. The process of claim 3 wherein the reactor inlet temperature is between about 37° C. and about 510° C. and the reactor pressure is between about 25 psig and 800 psig.

5. The process of claim 3 wherein the crystalline aluminosilicate zeolite or the product of thermal treatment thereof is combined in an amount between about 1 and about 99 weight percent in a binder therefor.

6. The process of claim 5 wherein said binder is alumina.

7. The process of claim 1 wherein the alkylating agent is an alcohol.

8. The process of claim 7 wherein the reactor inlet temperature is between about 200° C. and about 650° C. and the reactor pressure is between about 25 psig and 800 psig.

9. The process of claim 7 wherein the crystalline aluminosilicate zeolite or the product of thermal treatment thereof is combined in an amount between about 1 and about 99 weight percent in a binder therefor.

10. The process of claim 9 wherein said binder is alumina.

11. The process of claim 2 wherein the reactor inlet temperature is between about 340° C. and about 595° C. and the reactor pressure is between about 25 psig and 800 psig.

12. The process of claim 2 wherein the crystalline aluminosilicate zeolite or the product of thermal treatment thereof is combined in an amount between about 1 and about 99 weight percent in a binder therefor.

13. The process of claim 12 wherein said binder is alumina.

14. The process of claim 2 wherein the aromatic hydrocarbon charge is toluene and the transalkylating agent is trimethylbenzene.

15. The process of claim 2 wherein the aromatic hydrocarbon charge is toluene and the transalkylating agent is toluene.

* * * * *

UNITED STATES PATENT AND TRADEMARK OFFICE
CERTIFICATE OF CORRECTION

PATENT NO. : 4,136,128
DATED : January 23, 1978
INVENTOR(S) : WERNER O. HAAG and DAVID H. OLSON It is certified that error appears in the above-identified patent and that said Letters Patent are hereby corrected as shown below:

Column 18　Line 39　—　Delete "pressure"

Signed and Sealed this

Tenth Day of July 1979

[SEAL]

Attest:

Attesting Officer

LUTRELLE F. PARKER
Acting Commissioner of Patents and Trademarks